US009414029B2

(12) United States Patent
Miyazaki et al.

(10) Patent No.: US 9,414,029 B2
(45) Date of Patent: Aug. 9, 2016

(54) VIDEO CONTROL APPARATUS AND VIDEO CONTROL METHOD

(75) Inventors: Jungo Miyazaki, Kawasaki (JP); Yoshikatsu Ichimura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 657 days.

(21) Appl. No.: 13/241,066

(22) Filed: Sep. 22, 2011

(65) Prior Publication Data

US 2012/0075530 A1  Mar. 29, 2012

(30) Foreign Application Priority Data

Sep. 28, 2010  (JP) ................................ 2010-217190

(51) Int. Cl.
*A61B 5/02* (2006.01)
*H04N 7/18* (2006.01)
*A61B 5/0484* (2006.01)
*A61B 5/055* (2006.01)
*H04N 21/44* (2011.01)
*H04N 21/442* (2011.01)

(52) U.S. Cl.
CPC ............ *H04N 7/183* (2013.01); *A61B 5/04842* (2013.01); *A61B 5/055* (2013.01); *H04N 21/44* (2013.01); *H04N 21/44218* (2013.01)

(58) Field of Classification Search
CPC .... A61B 5/0482; A61B 5/0476; A61B 5/026; A61B 5/0484
USPC .......................................... 600/504, 544, 545
See application file for complete search history.

(56) References Cited

U.S. PATENT DOCUMENTS

| 4,149,716 | A | * | 4/1979 | Scudder | ............... A61B 5/0482 345/156 |
| 2002/0077534 | A1 | * | 6/2002 | DuRousseau | .................. 600/300 |
| 2004/0073129 | A1 | * | 4/2004 | Caldwell et al. | .............. 600/544 |
| 2006/0241373 | A1 | * | 10/2006 | Strychacz | ............. A61B 5/4076 600/407 |
| 2008/0281221 | A1 | * | 11/2008 | Greco | .................. A61B 5/0482 600/545 |

FOREIGN PATENT DOCUMENTS

JP    2004-191628    7/2004

OTHER PUBLICATIONS

Jin et al., Classification of motion direction perceived based on EEG, Control and Decision Conference 2008, pp. 4322-4325.*
Miyawaki et al., "Visual image reconstruction from human brain activity using a combination of multi-scale local image decoders", Neuron, 60, 915-929 (2008).

* cited by examiner

*Primary Examiner* — Michael Kahelin
*Assistant Examiner* — Tho Tran
(74) *Attorney, Agent, or Firm* — Canon U.S.A., Inc. IP Division

(57) ABSTRACT

A video control apparatus includes a video presenting unit configured to present a video to a viewer, a brain activity measuring unit configured to measure a brain activity of the viewer, a feature amount estimating unit configured to estimate a feature amount related to a direction and an amount of motion of a video perceived by the viewer based on data acquired by the brain activity measuring unit, and a video control unit configured to control a video to be displayed by the video presenting unit based on the feature amount.

10 Claims, 8 Drawing Sheets

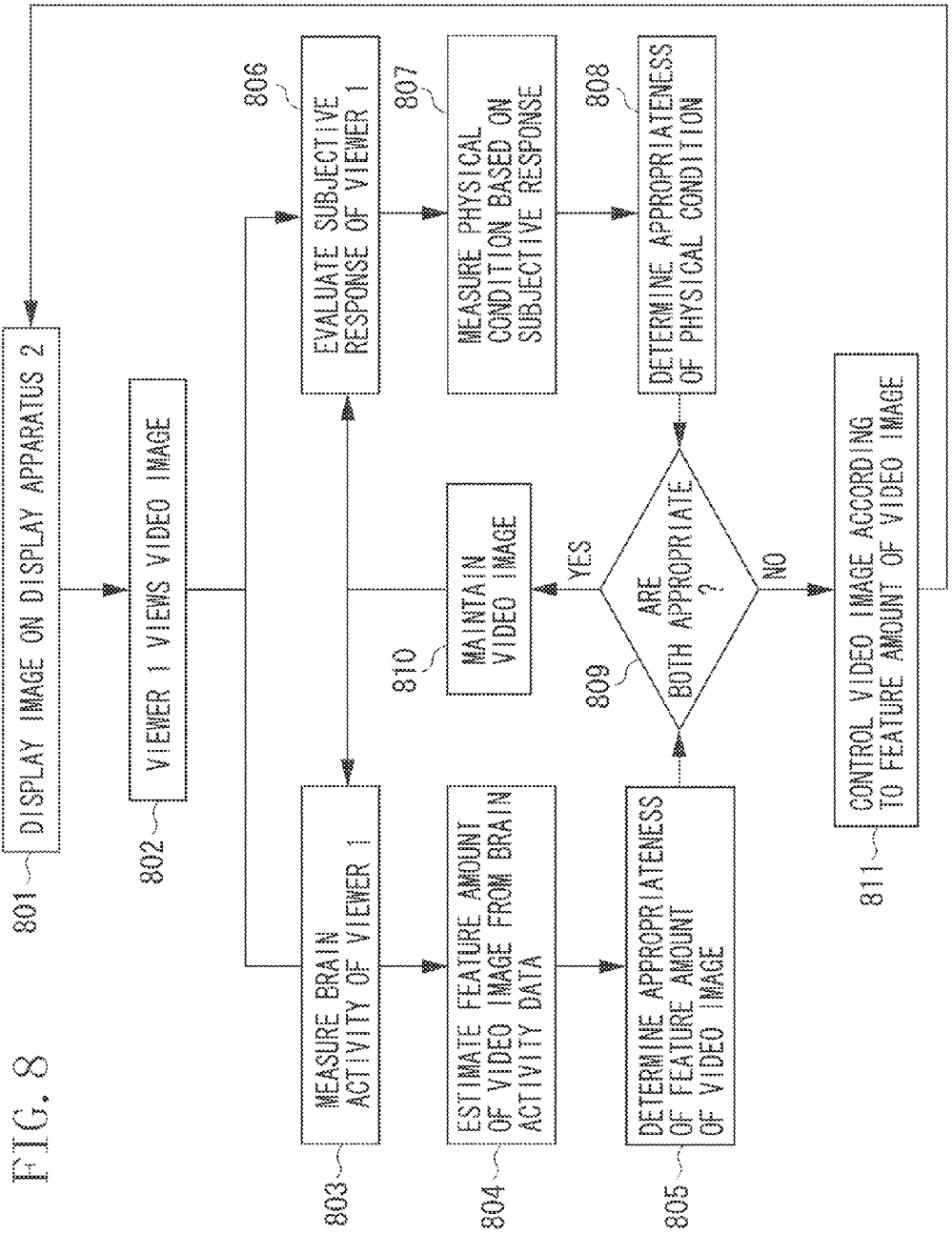

VIDEO CONTROL APPARATUS AND VIDEO CONTROL METHOD

BACKGROUND OF THE INVENTION

1. Field of the Invention

The present invention relates to a video control apparatus and a video control method which measure an influence on an organism by a video and control the video based on acquired data.

2. Description of the Related Art

In recent years, an increase in screen size and an enhancement in colorfulness in a video display apparatus has progressed, and a large number of viewers can enjoy videos having the sense of presence. While viewers have enjoyed videos, there have been reports of videos having a bad influence on an organism. For example, when a video photographed by means of a commercially-available video camera and having a camera shake is viewed through a large screen display, some viewers exhibit symptoms similar to motion sickness, that is, they have a discomfort which is referred to as a "visually induced motion sickness". In this scenario, the viewer has a feeling that the viewer is moving in a visual space through a video on a large screen which is being viewed while the viewer is stationary. Consequently, an inconsistency is made between a visual perception obtained from an optic organ and a sense of balance obtained from a vestibular organ so that a spatial cognition in the viewer's brain is hindered. In this condition, body control is impeded. The "visually induced motion sickness" is an example in which a component related to a motion in a video badly influences an organism.

While in some circumstances video has had unfavorable influences on organisms, in other circumstances, video has had favorable influences on organisms. For example, for infants, it is effective to view a video as a training for perceiving a visual stimulus, for example, a color, a shape or a motion. However, it is hard for an infant to express its own visual performance in a language. For this reason, it is difficult to evaluate whether a video which is being viewed is really perceived by the infant. Even if a mechanism for perceiving a motion of a video displays a video including a target moving at a high speed is displayed for an undeveloped infant, there is a possibility that the target might not be perceived and an advantage of the video might not be obtained. Therefore, the evaluation is hard to perform. For the purpose of promoting a development of the visual system of the infant, it is necessary to control a motion in a video at such a speed that the infant can perceive the motion. In consideration of the circumstances, there has been desired a technique for objectively detecting an influence of a video on an organism and controlling a video to be displayed for a viewer depending on the situation.

As the technique for changing a display condition, such as a display size or a resolution corresponding to a work progressing state of a user of a display apparatus or a fatigue situation corresponding thereto, and reducing the load on the organism of the user, Japanese Patent Application Laid-Open No. 2004-191628 discusses a display system and a display method which use organism-specific information. This system and method controls a display size of a character or an image, or a resolution or a display position, based on measured data on organism-specific information such as brain waves, respiration, a pulse, or blood pressure generated from an organism. The data reflecting a state of a user is stored in an apparatus for displaying a character or an image.

A technique for measuring a brain activity of a person viewing a video and analyzing acquired data to estimate a line segment in the video perceived by the viewer is discussed in Yoichi Miyawaki et al. "Visual image reconstruction from human brain activity using a combination of multi-scale local image decoders", Neuron, 60, 915-929 (2008). As discussed in this document, a nerve cell responding to a specific line segment in a video which is being viewed is present in the visual cortex of a human cerebrum. For example, in a primary visual cortex, the nerve cells are regularly arranged depending on visual fields of which the nerve cells take charge respectively. By measuring a neural activity of the primary visual cortex of a person viewing a video through functional magnetic resonance imaging, it is possible to estimate any position in the visual field in which an image of any line segment is displayed.

In the technique discussed in Japanese Patent Application Laid-Open No. 2004-191628, it did not estimate nothing about the movie factor which had influences on the organism-specific information, such as brain waves, a respiration, a pulse, blood pressure of viewer. For this reason, a video which does not need to be controlled is controlled in the same manner in addition to a video to be controlled. Consequently, an amount of information is unnecessarily reduced. As a result, there is an issue in that the quality of a video is unnecessarily deteriorated.

In the technique discussed in Yoichi Miyawaki et al. "Visual image reconstruction from human brain activity using a combination of multi-scale local image decoders", Neuron, 60, 915-929 (2008), it is possible to estimate sensory information of a viewer. However, no control is applied to a video being viewed based on the sensory information, and thus, the influence on the viewer cannot be controlled.

SUMMARY OF THE INVENTION

According to an aspect of the present invention, a video control apparatus includes a video presenting unit configured to present a video to a viewer, a brain activity measuring unit configured to measure a brain activity of the viewer, a feature amount estimating unit configured to estimate a feature amount related to a direction and an amount of motion of a video perceived by the viewer based on data acquired by the brain activity measuring unit, and a video control unit configured to control a video to be displayed by the video presenting unit based on the feature amount.

According to another aspect of the present invention, a video control method includes presenting a video to a viewer, measuring a brain activity of the viewer, estimating a feature amount related to a direction and an amount of motion of a video perceived by the viewer based on data related to the measured brain activity, and controlling a video to be displayed for the viewer based on the feature amount.

According to an exemplary embodiment of the present invention, a feature amount related to a motion of a video which influences a viewer can be estimated through the measurement of a brain activity. Therefore, it is possible to control a video image effect based on the feature amount.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 8 is a flowchart illustrating a video control method according to the third exemplary embodiment.

DESCRIPTION OF THE EMBODIMENTS

Various exemplary embodiments, features, and aspects of the invention will be described in detail below with reference to the drawings.

A video control apparatus and a video control method according to exemplary embodiments of the present invention estimate a motion vector, which is a feature amount related to a motion of a video, from a brain activity of a viewer that is viewing the video, and control the video.

Figure 1:
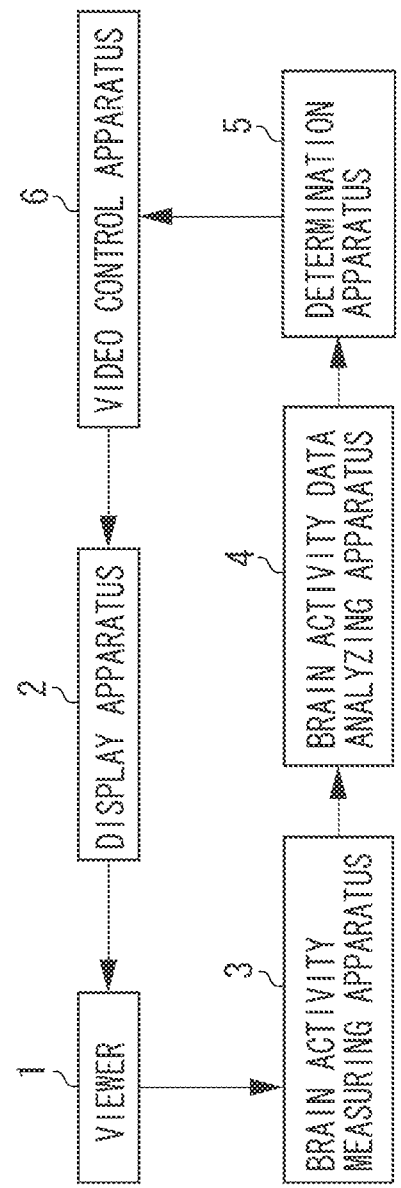
FIG. 1 is a block diagram illustrating a basic structure of a video control apparatus according to a first exemplary embodiment of the present invention.

FIG. 1 is a block diagram illustrating a basic structure of a video control apparatus according to a first exemplary embodiment of the present invention.

A brain activity obtained when a viewer 1 sees a video displayed by a display apparatus 2, which is a video presenting unit, is measured by a brain activity measuring apparatus 3, which is a brain activity measuring unit. Examples of an apparatus to be used for the brain activity measuring apparatus 3 include various brain activity measuring apparatuses such as a functional magnetic resonance imaging apparatus, a positron emission tomography (PET) apparatus, a near-infrared spectroscopy apparatus, an electroencephalograph, a magneto-encephalograph, and a neural activity recording apparatus using an electrode. In particular, the functional magnetic resonance imaging can measure an activated region in the cerebral cortex with high sensitivity and precision. The PET apparatus also measures the activity of a specific brain region with high precision. The electroencephalograph and the near-infrared spectroscopy apparatus can acquire a signal following a brain activity using a simple structure for attaching a measuring sensor to a predetermined portion of the head of a subject.

Data on the brain activity measured by the brain activity measuring apparatus 3 is transmitted to a brain activity data analyzing apparatus 4, which is a feature amount estimating unit, so that a motion vector of a video, which is a feature amount of a video perceived by the viewer 1, is estimated. The motion vector of the video is one of dynamic image data expressing methods. When a still image corresponding to a certain moment of a moving image is set to be a reference, a motion component between the still image and other still images corresponding to moments before and after the reference is expressed as a vector. Discomfort known as "visually induced motion sickness" is correlated with a motion vector of a video. In order to detect the "visually induced motion sickness", it is effective to estimate the motion vector of the video.

More specifically, a signal is acquired following the activity of a nerve cell which selectively responds to a moving direction and speed of a video being viewed. It is known that the nerve cell is present in specific visual areas in the cerebral cortex and is arranged in a corresponding rule to a position in a visual field. In the case of the electroencephalograph, the magneto-encephalograph and the neural activity recording apparatus using an electrode, electrical activity of the nerve cell, which is induced by video viewing, is measured. In the case of the functional magnetic resonance imaging apparatus, the PET apparatus, and the near-infrared spectroscopy apparatus, a change in cerebral blood flow, which is caused by the electrical activity of the nerve cell that is induced by the video viewing, is measured. The brain activity measuring apparatuses acquire, as an activity pattern, a location and an activity level of the nerve cell, which vary depending on a two-dimensional image projected onto a retina of the viewer 1 every second.

For example, by presenting to the viewer 1 a video having a random moving dot pattern while varying increasing the speed and measuring the activity of the nerve cell, it is possible to obtain as the activity pattern the location and the activity level of the nerve cell which selectively responds to the random dot pattern. By presenting a random moving dot pattern while increasing or decreasing the speed and measuring a neural activity of the viewer 1, it is possible to acquire, as the activity pattern, the location and the activity level of the nerve cell which selectively responds to a predetermined moving direction and speed. By carrying out a pattern recognition processing over the neural activity pattern varied with a simple motion in a video and the neural activity pattern of the viewer 1 which is measured in optional video viewing, it is possible to quantitatively estimate a direction and a speed of a visual motion included in the neural activity pattern.

An estimated value of a motion vector of a video is transmitted to a determination apparatus 5. The determination apparatus 5 determines whether control for a video is necessary based on the value of the motion vector. In order to effectively carry out the determination, it is possible to preset a threshold of the value of the motion vector. For example, a critical value of a motion vector which causes the "visually induced motion sickness" or a necessary reference value for giving an intended video image effect is set. In consideration of the case in which the "visually induced motion sickness" is determined, if the value of the motion vector exceeds the preset threshold, it is determined that a video perceived by the viewer 1 is not appropriate, that is, a risk of the "visually induced motion sickness" is increased, and a signal for suppressing the video image effect is output to a video control apparatus 6.

In the case in which the risk of the "visually induced motion sickness" is increased, the random dot pattern is superimposed on a video to decrease a sensation of motion in a specific direction which is perceived by a viewer based on a perception characteristic of the viewer that is previously measured.

More specifically, a random dot pattern is generated and superimposed in a video to output a signal to the video control apparatus 6 to decrease the sensation of the motion in the specific direction which is perceived by the viewer.

It is presumed that perception for a motion of a video varies from person to person. For this reason, it is useful if the perception is regulated in advance for each viewer. For example, a part of the video is presented to a viewer and brain activity in that case is measured to estimate a motion vector of the video. A random moving dot pattern depending on the motion vector of the video thus estimated is superimposed on the video and the brain activity in that case is measured to obtain a neural activity pattern responding to the motion of the video. Then, a speed, a color, or the number of dots is varied for the same video and the random dot pattern is repetitively presented, and the brain activity is measured every time to acquire a neural activity pattern. At the same time, referring to the motion of the video on which the random dot pattern is superimposed, the viewer provides a subjective impression. By initially carrying out the above-described procedure, it is possible to obtain a degree of the sensation of the motion that is to be perceived by the viewer to a video on which a random dot pattern having a different attribute is superimposed and any neural activity pattern to be presented. In other words, it is possible to regulate the attribute of the random dot pattern to be superimposed by previously measuring the perception characteristic of the viewer to a video. Therefore, it is possible to obtain an advantage that video control can be carried out more appropriately.

When the value of the motion vector does not exceed the threshold, it is determined that the risk of the "visually induced motion sickness" is small, and a signal is not output to the video control apparatus 6. The threshold can be optionally set in consideration of a sensitivity of the viewer 1 to a video. It is more useful to previously examine a motion vector of a video estimated from the measurement of a brain activity and an influence of the video on the viewer in that case. A questionnaire method related to the measurement of the brain activity in video viewing and a subjective impression is executed by taking a plurality of viewers as a target. It is desirable to set an appropriate threshold for the motion vector of the video based on a result of the value of the motion vector of the video which is estimated from the measurement of the brain activity and the subjective impression of the viewer.

In the case in which the sensation of the motion to be given to the viewer 1 by the video is to be increased, it can be determined that an intended video image effect is insufficient and is inappropriate if the value of the motion vector does not exceed a preset reference value, and a signal is output to the video control apparatus 6 to more greatly increase the video image effect. More specifically, a random dot pattern is generated in a video and a signal is output to the video control apparatus 6 to cause the random dot pattern to carry out a motion depending on the motion vector estimated from the measurement of the brain activity. As described above, it is possible to carry out appropriate video control for the viewer by previously measuring a perception characteristic to a motion of a video which is varied on a viewer-by-viewer basis. If it is determined that the intended video image effect is not given to the viewer, the random dot pattern is superimposed on the video to increase a sensation of a motion in a specific direction based on a perception characteristic of the viewer which is previously measured.

In the case where the value of the motion vector exceeds the reference value, it is determined that the video image effect is sufficient, that is, a video perceived by the viewer 1 is appropriate, and a signal is not output and the video is maintained.

For the display apparatus 2, which is a video presenting unit, it is possible to use every display apparatus which can be usually considered. For example, a display apparatus including a cathode-ray tube or a liquid crystal panel, a projection type display apparatus, or a head mount type display apparatus. In the case in which the brain activity measuring apparatus 3 is influenced, the display apparatus 2 is limited. In the case in which the magnetic resonance imaging apparatus is used as the brain activity measuring apparatus 3, a system including a screen disposed in a visual field of a viewer and a video projector for projecting a video onto the screen at the outside of the magnetic resonance imaging apparatus is useful for the display apparatus 2.

It is possible to record an output history of a perception characteristic of the viewer on a storage medium such as a hard disk or a semiconductor memory which is provided in the determination apparatus 5 or the video control apparatus 6. The output history is stored with an identifier (ID) for each viewer. When the viewer views the video again, the output history with an ID corresponding to the viewer is read from the storage medium. Even if the measurement of the brain activity is not carried out, the same video control can be performed. By carrying out the measurement for each viewer once, it is possible to obtain an effect for viewing a video subjected to appropriate control without a restraint due to the measurement of the brain activity.

In the first exemplary embodiment, there is described an example in which a motion vector, which is a feature amount related to a motion of a video, is estimated from a brain activity of a person viewing the video and the video is thus controlled.

In the present exemplary embodiment, the brain activity measuring apparatus 3 employs functional magnetic resonance imaging (an fMRI apparatus). The display apparatus 2 includes a screen provided in a cylindrical measuring portion in the brain activity measuring apparatus 3 and a liquid crystal projector disposed on an outside of the measuring portion and serving to project a video onto the screen.

Figure 2:
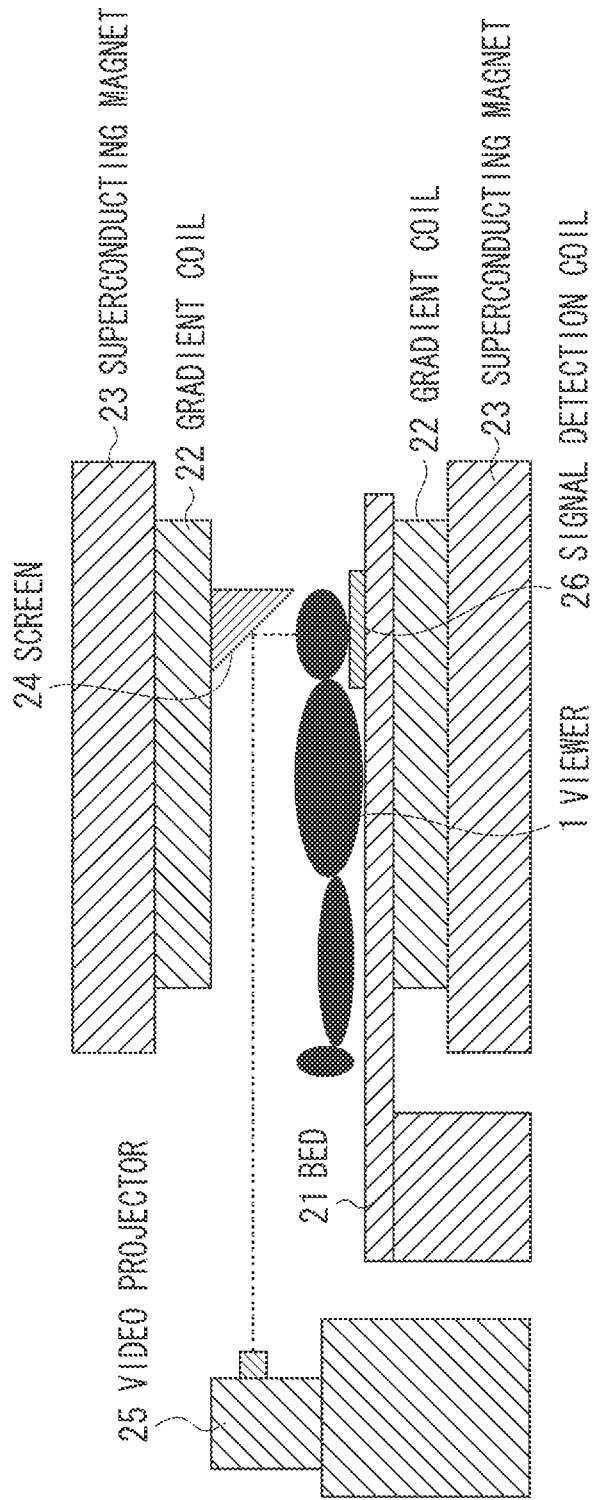
FIG. 2 is a sectional view illustrating a specific structure of a brain activity measuring apparatus according to the first exemplary embodiment.

FIG. 2 is a sectional view illustrating the brain activity measuring apparatus 3 according to the present exemplary embodiment. The viewer 1 lays upon a bed 21 attached to the fMRI apparatus and is placed in a cylindrical measuring portion provided with a gradient coil 22 and a superconducting magnet 23. A screen 24 is provided in the measuring portion and is located in front of the viewer's 1 eyes, and displays a video projected from outside the measuring portion by a video projector 25, such as liquid crystal projector. A signal detecting coil 26 is provided behind the viewer's 1 head and detects an electromagnetic signal correlated to a change in cerebral blood flow associated with neural activity.

Figure 3:
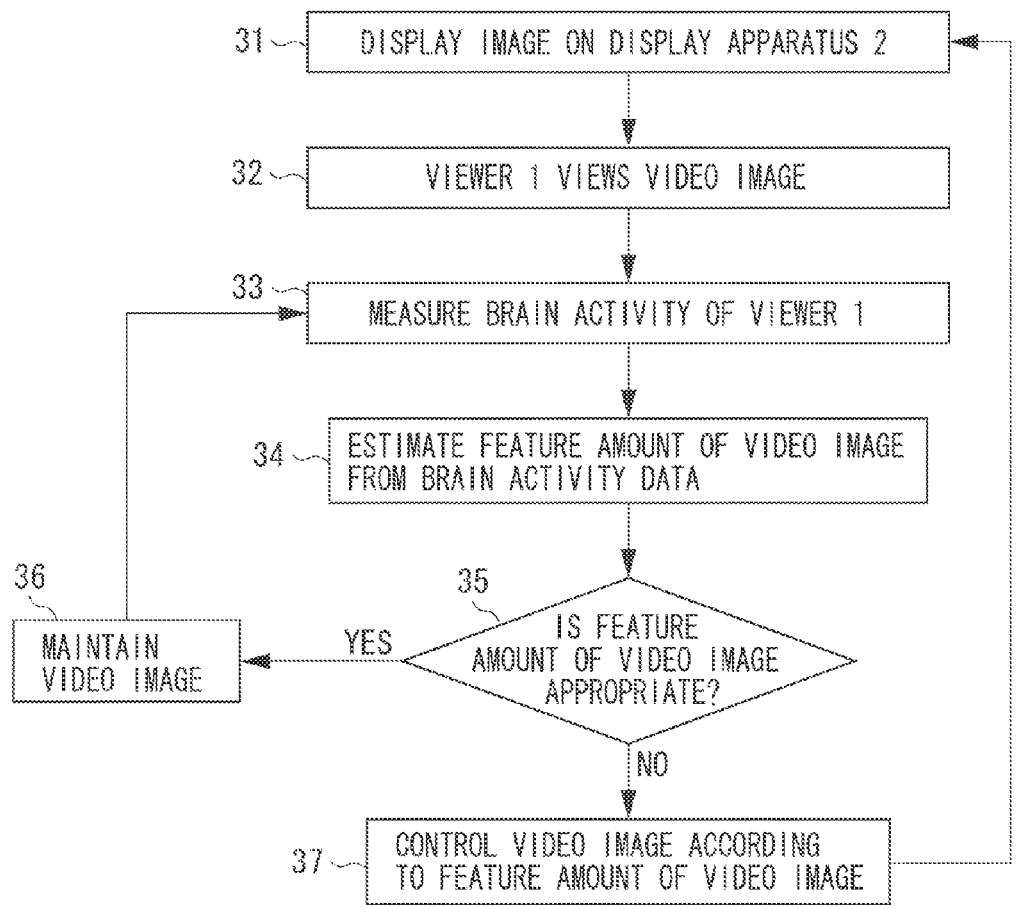
FIG. 3 is a flowchart illustrating a video control method according to the first exemplary embodiment.

FIG. 3 is a flowchart illustrating a video control method according to the present exemplary embodiment. In the present exemplary embodiment, a video is displayed for a viewer 1 on the display apparatus 2 (shown as 31 in FIG. 3.) The viewer 1 begins to view the video (shown as 32 in FIG. 3), and the viewer's 1 brain activity begins to be measured using the fMRI apparatus (shown as 33 in FIG. 3.) The brain region to be measured in the present exemplary embodiment is set to be a middle temporal area (MT).

Figure 4:
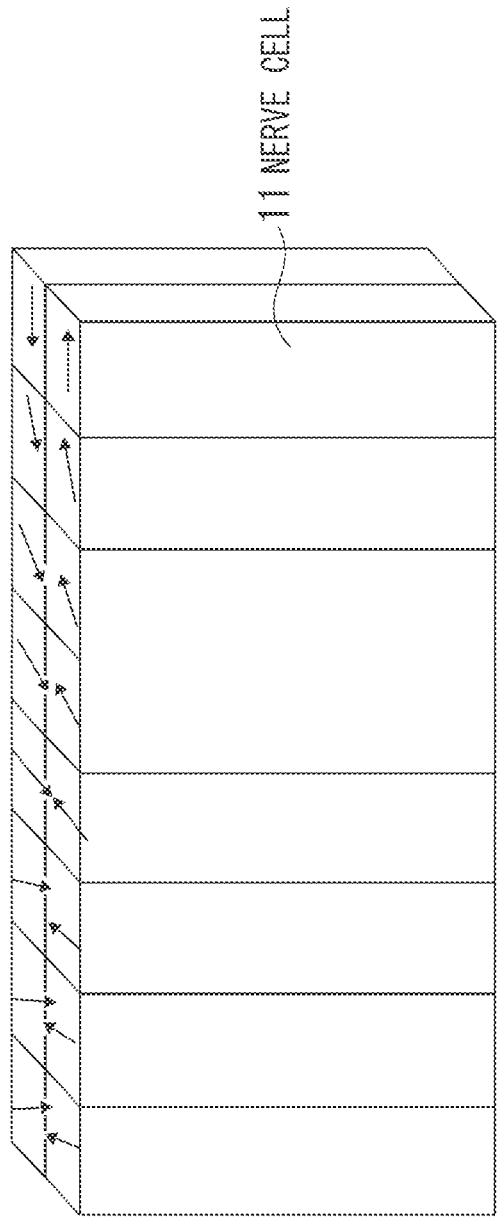
FIG. 4 is a typical view illustrating a nerve cell having a visual moving direction selectivity.

FIG. 4 (prior art) is a typical view illustrating a nerve cell having a visual moving direction selectivity in the middle temporal area. As illustrated in FIG. 4, a nerve cell responding selectively to a moving direction of a video is present in the middle temporal area is known (see Yoichi Miyawaki et al. "Visual image reconstruction from human brain activity using a combination of multi-scale local image decoders", Neuron, 60, 915-929 (2008)). The nerve cell having the visual moving direction selectivity is illustrated as a column in FIG. 4, and an arrow illustrated on an upper surface thereof indicates a moving direction in a video to which each nerve cell selectively responds.

For example, a nerve cell 11 in FIG. 4 acts when the video includes a target moving in a rightward direction, and does not act to a target moving in other directions. It is known that the nerve cells are regularly arranged to correspond to a special disposition projected onto a retina. By measuring the activity of the nerve cells with the use of the fMRI apparatus, it is possible to obtain a neural activity pattern corresponding to whether the viewer 1 perceives any video moving in any direction at any position in the visual field. It is also known that nerve cells indicate different activity patterns depending on a speed of an object moving in a video. Thus, it is apparent that the neural activity pattern corresponds to a motion vector in a video which is perceived.

Although the brain activity pattern in the middle temporal area is measured in the present exemplary embodiment, the nerve cell responding selectively to the motion of the video is also present in a primary temporal area, a secondary temporal area and a medial superior temporal (MST) area. By setting at least one of them to be a measuring target, it is possible to obtain the same advantage.

The remaining sequence of FIG. 3 follows. Brain activity data of the viewer 1 measured by the fMRI apparatus is transmitted to the brain activity data analyzing apparatus 4. Brain activity data analyzing apparatus 4 estimate feature amount of video image from the brain activity (shown as 34 in FIG. 3.) The brain activity data analyzing apparatus 4 analyzes the brain activity data and calculates the extent to which the video activates nerve cells in any area being measured, and stores the information as a brain activity pattern. As described above, the brain activity pattern corresponds to an activity state of the nerve cell(s) having a selectivity for a moving direction and a speed of the video, that is, a motion vector of the video which is perceived by the viewer 1. The brain activity pattern to be measured is varied depending on the motion of the video to be displayed. Therefore, it is possible to carry out pattern recognition processing over the brain activity pattern, thereby estimating a motion component of a video which is perceived from the brain activity pattern, that is, a motion vector of the video. For example, by implementing the brain activity data analyzing apparatus 4 as a support vector machine which is previously trained, it is possible to further improve a pattern recognizing performance and to enhance precision in a motion vector of the video which is estimated.

A value of a motion vector of a video which is estimated by the brain activity data analyzing apparatus 4 is transmitted to the determination apparatus 5. The determination apparatus 5 determines whether control for a video is necessary based on the value of the motion vector (shown as 35 in FIG. 3.) In the determination apparatus 5, it is possible to preset the threshold of the value of the motion vector. For example, a critical value of a motion vector which causes the "visually induced motion sickness" or a necessary reference value for giving an intended video image effect can be set. Consider the following example in which the "visually induced motion sickness" is determined.

If the value of the motion vector exceeds the preset threshold, it is determined that a video perceived by the viewer 1 is not appropriate, that is, a risk of the "visually induced motion sickness" is increased, and a signal is output to the video control apparatus 6 (shown as 37 in FIG. 3.) As a result, a sensation of a motion causing the "visually induced motion sickness" is suppressed.

When the value of the motion vector does not exceed the preset threshold, that is, the video perceived by the viewer 1 is present within an appropriate range, it is determined that there is a small risk of the "visually induced motion sickness", and a signal is not output and the video is maintained (shown as 36 in FIG. 3.)

Moreover, there will be considered the case in which the sensation of the motion given to the viewer 1 by the video is increased.

When it is determined that the value of the motion vector of the video does not satisfy the preset reference value by determination apparatus 5 (shown as 35 in FIG. 3), that is, a video image effect is insufficient, a random dot pattern is superimposed to enhance the sensation of the motion given by the video so that a sensation of a motion in a specific direction which is perceived by the viewer 1 can be increased (shown as 37 in FIG. 3.)

Next, a description will be provided with respect to a video control apparatus including a physiological response measuring unit according to a second exemplary embodiment of the present invention.

Figure 5:
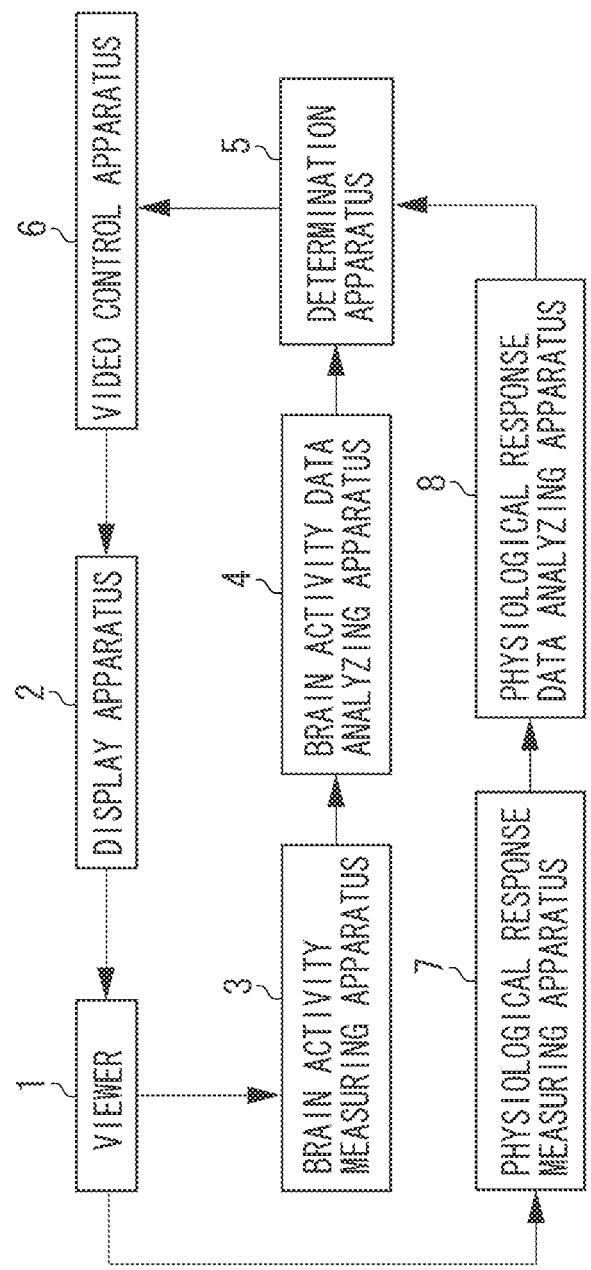
FIG. 5 is a block diagram illustrating a basic structure of a video control apparatus including a physiological response measuring unit according to a second exemplary embodiment of the present invention.

FIG. 5 is a block diagram illustrating a basic structure of a video control apparatus according to the second exemplary embodiment. A brain activity of a viewer 1 that is viewing a video displayed on a display apparatus 2 is measured by using a brain activity measuring apparatus 3. In the same manner as in the first exemplary embodiment, the acquired brain activity data is analyzed to estimate a feature amount related to a motion of the video, thereby controlling the video. The present exemplary embodiment, includes a physiological response measuring apparatus 7 for measuring an influence of the video on an autonomic nervous system of the viewer 1. For example, it is known that the autonomic nervous system is in an abnormal condition when discomfort associated with "visually induced motion sickness" occurs. As described in the first exemplary embodiment, it is possible to estimate an influence of a video on an organism by measuring brain activity. The present exemplary embodiment's ability to measure a physiological index of the autonomic nervous system is effective for improving the temporal control of video more precisely because it enables to objectively specify the time when video had an influence on viewer. Herein, it is presumed that an electrocardiograph and a respirometer are used as the physiological response measuring apparatus 7, while the other structures are the same as those in the first exemplary embodiment.

Figure 6:
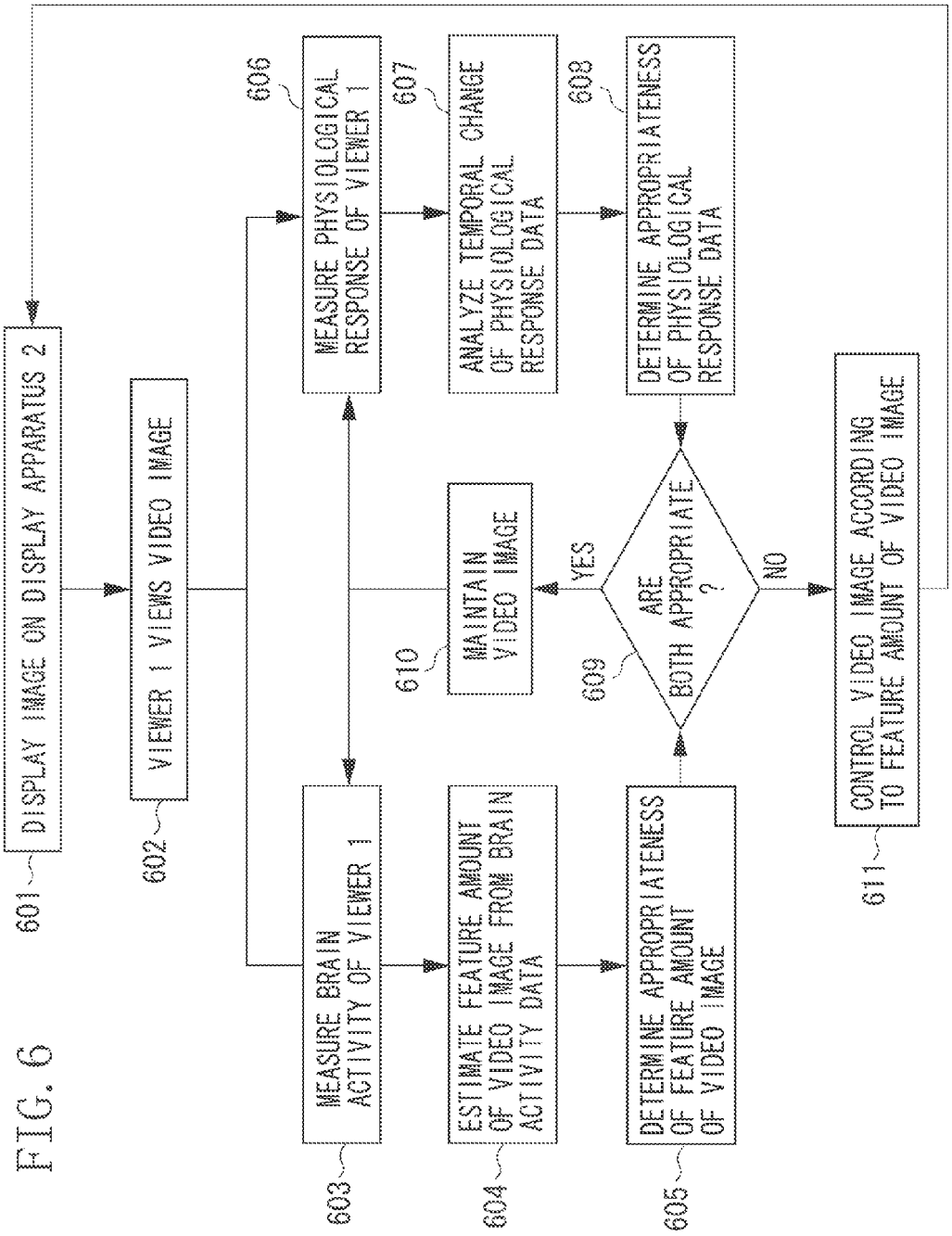
FIG. 6 is a flowchart illustrating a video control method according to the second exemplary embodiment of the present invention.

FIG. 6 is a flowchart illustrating a video control method according to the second exemplary embodiment. The viewer 1 lays upon a bed 21 in a measuring portion of an fMRI apparatus and views a video projected onto a screen 24 located in front of the viewer's 1 eyes (shown as 601 and 602 in FIG. 6.) At that time, brain activity is measured by the fMRI apparatus to obtain a brain activity pattern in a predetermined region of the viewer's brain (shown as 603 in FIG. 6.) A brain activity data analyzing apparatus 4 analyzes the brain activity pattern and estimates a feature amount related to a motion of a video which is perceived by the viewer 1, that is, a motion vector (shown as 604 in FIG. 6.)

The physiological response measuring apparatus 7, which includes a an electrocardiograph and respirometer, measures the viewer's 1 heart rate and a respiration rate while the viewer 1 views the video (shown as 606 in FIG. 6.) The acquired data is transmitted to a physiological response data analyzing apparatus 8 and is recorded as time series data. The physiological response data analyzing apparatus 8 calculates a temporal change in the data and analyzes a dynamic characteristic of data for a measuring period. For example, increase, decrease or constant, and outputs the result to a determination apparatus 5 (shown as 607 in FIG. 6.)

The determination apparatus 5 determines whether the value of the motion vector perceived by the viewer 1, input from the brain activity data analyzing apparatus 4, and time variations in the heart rate and the respiration rate of the viewer 1 input from the physiological response data analyzing apparatus 8 are within an appropriate range (shown as 605, 608, and 609 in FIG. 6.) When neither the value of the motion vector nor the time variations in the heart rate and the respiration rate exceed a preset threshold, it is determined that the video perceived by the viewer 1 is appropriate, and a signal is not output and the video is maintained (shown as 610 in FIG. 6.) When the value of the motion vector or the time variation in the heart rate or the respiration rate exceeds the preset threshold, it is determined that the video perceived by the viewer 1 is not appropriate, that is, a risk of the "visually induced motion sickness" is increased, and a signal is output to a video control apparatus 6 (shown as 611 in FIG. 6.)

The video control apparatus 6 receiving the signal superimposes a random moving dot pattern to suppress a sensation of a motion given to the viewer 1 by the video based on the motion vector of the video which is input from the brain activity data analyzing apparatus 4 to the display apparatus 2.

In the case in which the amount of the motion of the video exceeds a predetermined value so that the amount of the motion vector cannot be reduced fully even if the random dot pattern is superimposed, a negative influence on the viewer can be prevented by including processing as will be described below. In the case in which the occurrence of the "visually induced motion sickness" is predicted because the amount of the motion vector cannot be reduced fully, the projection of the video onto the screen 24 is stopped to suppress the sensation of the motion given to the viewer 1 by the video. Alternatively, it is also possible to switch to a prepared still image or a video having a small motion, and to present either to the viewer 1.

Examples of a method of determining a predetermined value of the amount of the motion can include measuring an amount of a motion vector in which a negative influence begins to appear and determining the predetermined value to be 1.5 times as great as a value of a motion vector which is usually calculated in viewing a video in which the "visually induced motion sickness" is not caused.

According to the structure of the present exemplary embodiment, it is possible to specify a time that an alteration of a physiological response appears. Therefore, it is also possible to identify the motion vector of the video perceived by the viewer 1 at that time. Accordingly, it is also possible to specify a motion component of a video which negatively influences an organism and to carry out erasure or editing, thereby performing control into a safe video.

While the physiological response measuring apparatus 7 of the present exemplary embodiment has been described to include an electrocardiograph and respirometer, it is not limited to the use of these two devices. For example, other noninvasive physiological response measuring units, such as a sphygmomanometer, an electromyogram, a plethysmograph, an electrodermogram, a sweating rate meter, an electrogastrography and an electrooculography can also be used. A particular measuring apparatus is attached to a respective part of a viewer's 1 body and acquires a time series biological signal reflecting an action of a sympathetic nervous system and a parasympathetic nervous system. For example, it is possible to introduce a pulse monitor in place of the electrocardiograph. While the respirometer detects a perimeter change of a trunk of a body, e.g., the abdomen or breast, by means of an adjustable elastic resistance element and calculates a breathing rate or an amount of ventilation, the pulse monitor irradiates a near infrared ray onto a finger tip to detect a blood flow in a peripheral blood vessel, thereby calculating a pulse rate or a time interval between pulses from an output waveform. The pulse rate or the time interval between the pulses reflects a heart rate variability and can acquire an equivalent signal to a biological signal obtained from the electrocardiograph. The respirometer and the pulse monitor have simple structures and apply a small load to a subject, and also make a small electromagnetic noise to the fMRI apparatus. Accordingly, it is possible to obtain an advantage that a burden to the viewer 1 in the fMRI apparatus can be reduced and the physiological response can be measured more precisely.

Next, a description will be provided with respect to a video control apparatus including a subjective assessment unit according to a third exemplary embodiment of the present invention.

Figure 7:
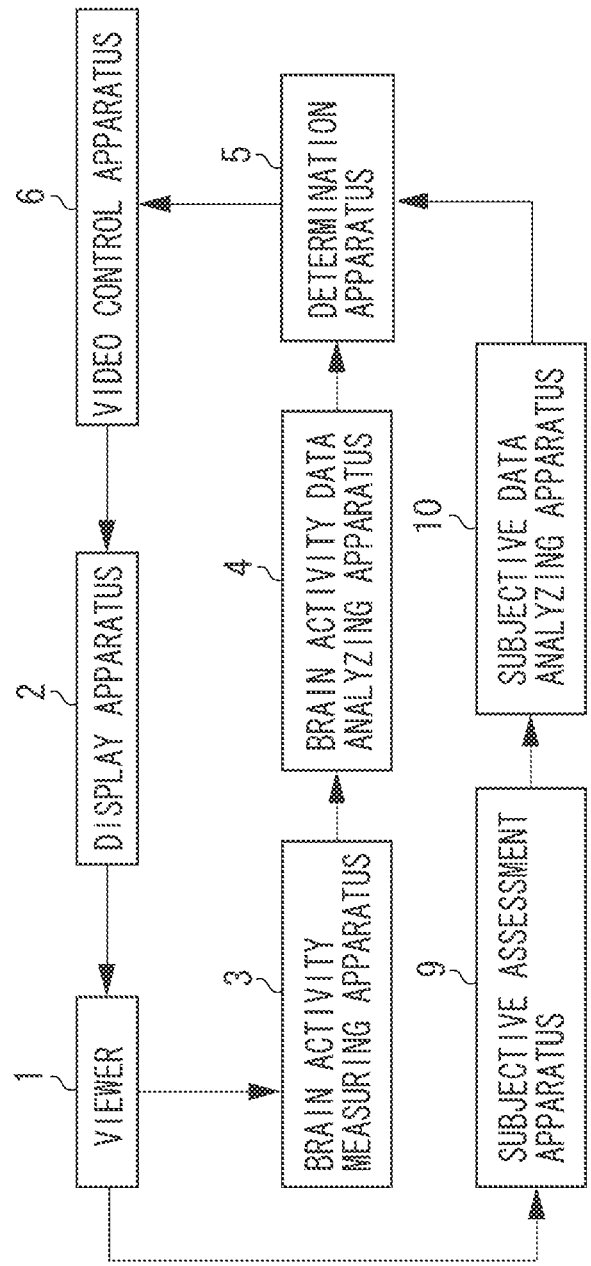
FIG. 7 is a block diagram illustrating a basic structure of a video control apparatus including a subjective assessment unit according to a third exemplary embodiment of the present invention.

FIG. 7 is a block diagram illustrating a basic structure of a video control apparatus according to the third exemplary embodiment. The structure of the present exemplary embodiment is similar to that of the second exemplary embodiment, but with the physiological response measuring unit being replaced with the subjective assessment unit. According to the present exemplary embodiment, the present exemplary embodiment is characterized by a subjective assessment apparatus 9 for evaluating a subjective response related to a physical condition from the viewer 1 in place of the measurement for the condition of the autonomic nervous system of the viewer 1 through the physiological response measuring apparatus 7 in the second exemplary embodiment.

FIG. 8 is a flowchart illustrating a video control method according to the third exemplary embodiment. The viewer 1 views a video displayed on a display apparatus 2 (shown as 801 and 802 in FIG. 8) and a brain activity of the viewer 1 is measured by using a brain activity measuring apparatus 3 (shown as 803 in FIG. 8.) In the same manner as in the first exemplary embodiment, brain activity data is acquired and analyzed to estimate a feature amount related to a motion of a video and the video is thus controlled (shown as 804 in FIG. 8.) The present exemplary embodiment includes the subjective assessment apparatus 9, which is provided with a push button (not shown) that allows the viewer 1 to intentionally indicate an alteration of the viewer's 1 own physical condition (shown as 806 in FIG. 8.) More specifically, the viewer 1 holds the subjective assessment apparatus 9, and if the viewer 1 experiences any discomfort when viewing the video, the viewer 1 pushes the push button. Herein, setting is carried out in such a manner that a degree of the discomfort is expressed depending on the number of times the push button is pushed. Every time the viewer 1 pushes the push button, the subjective assessment apparatus 9 outputs a signal to a subjective data analyzing apparatus 10. The subjective data analyzing apparatus 10 counts the signals and analyzes the degree of the discomfort which is indicated by the viewer 1, and outputs a signal to the determination apparatus 5 (shown as 807 in FIG. 8.)

The determination apparatus 5 determines whether the value of the motion vector perceived by the viewer 1, input from the brain activity data analyzing apparatus 4 and a subjective assessment value input from the subjective data analyzing apparatus 10 are within an appropriate range (shown as 805, 808, and 809 in FIG. 8.) When neither the value of the motion vector nor the subjective assessment value exceed a preset value, it is determined that the video perceived by the viewer 1 is appropriate, and a signal is not output and the video is maintained (shown as 810 in FIG. 8.) When either the value of the motion vector or the subjective assessment value exceeds a preset value, it is determined that the video perceived by the viewer 1 is not appropriate, that is, a risk of a "visually induced motion sickness" is increased, and a signal is output to a video control apparatus 6 (shown as 811 in FIG. 8.)

The video control apparatus 6, in response to receiving the signal, superimposes a random moving dot pattern to suppress a sensation of a motion given to the viewer 1 by the video based on the motion vector of the video which is input from the brain activity data analyzing apparatus 4 to the display apparatus 2. If it is determined that the "visually induced motion sickness" is serious, a video control signal is output to the video projector 25 to stop the projection of a video onto the screen 24, thereby suppressing the sensation of the motion given to the viewer 1 by the video. Alternatively, it is possible to switch to a prepared still image or a video having a small motion and to present either to the viewer 1.

The present exemplary embodiment has been described with one example of for the subjective assessment unit. Any other method of obtaining a subjective assessment from the viewer 1 that is applicable. For example, by introducing a questionnaire method of Simulator Sickness Questionnaire (SSQ) during a measurement, it is possible to evaluate the subjectivity of a viewer in more various scales, such as a headache or an eye strain in addition to the presence of the discomfort. See for example Kennedy et al. "Simulator sickness questionnaire: an enhanced method for quantifying simulator sickness", International Journal of Aviation Psychology, 3(3):203-220 (1993). It is also possible to select a desirable one of questionnaires set through the SSQ and to cause the viewer to answer the same.

While the second exemplary embodiment employs only includes the physiological response measuring unit and the third exemplary embodiment only includes the subjective assessment unit, in yet another exemplary embodiment, it is possible to measure the condition of viewer's mind and body by employing a structure in which both are provided. Consequently, it is possible to estimate a point of time that a video mainly influences the viewer. Accordingly, it is possible to produce an advantage that a video image effect to be given to the viewer can be controlled more accurately.

Aspects of the present invention can also be realized by a computer of a system or apparatus (or devices such as a central processing unit (CPU) or a micro processing unit (MPU)) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-217190 filed Sep. 28, 2010, which is hereby incorporated by reference herein in its entirety.

What is claimed is:

1. A video control apparatus comprising:
   a video presenting unit configured to present a video to a viewer;
   a brain activity measuring unit configured to measure a brain activity of the viewer to acquire an activity pattern based on the brain activity of the viewer during viewing of the video by the viewer;
   one or more processors; and
   one or more computer-readable media storing one or more programs, the one or more programs comprising instructions that, when executed by the one or more processors, cause the one or more processors to perform operations comprising:
   estimating a motion vector which comprises a direction and a speed of visual motion in the video perceived by the viewer, wherein the estimating the motion vector comprises performing pattern recognition processing based on the acquired activity pattern; and
   controlling a video to be displayed by the video presenting unit based on the estimated motion vector.

2. The video control apparatus according to claim 1, the operations further comprising decreasing or increasing a speed of visual motion of the video in the direction comprised in the estimated motion vector.

3. The video control apparatus according to claim 1, further comprising at least one of a physiological response measuring unit configured to measure a response of an autonomic nervous system of the viewer and a subjective assessment unit configured to evaluate a subjective response related to a physical condition of the viewer.

4. The video control apparatus according to claim 3, wherein the physiological response measuring unit includes a sensor to detect signals related to at least one of a blood pressure, a heart rate, a myogenic potential, a pulse, a respiration, a skin conductance, a perspiration, a gastric potential, and an eye movement.

5. The video control apparatus according to claim 1, wherein the brain activity measuring unit includes at least one of a functional magnetic resonance imaging apparatus, a positron emission tomography apparatus, a near-infrared spectroscopy apparatus, an electroencephalograph, a magneto-encephalograph, and a neural activity recording apparatus using an electrode.

6. The video control apparatus according to claim 1, the operations further comprising stopping presentation of the video, displaying a still image, or presenting another video when the speed of the visual motion in the video comprised in the estimated motion vector exceeds a predetermined value.

7. A video control method comprising:
   presenting a video to a viewer;
   measuring brain activity of the viewer to acquire an activity pattern based on the brain activity of the viewer during viewing of the video by the viewer;
   estimating a motion vector which comprises a direction and a speed of visual motion in the video perceived by the viewer, using a processing unit that is programmed to estimate the motion vector, wherein the estimating the motion vector comprises performing pattern recognition processing based on the acquired activity pattern; and
   controlling a video to be displayed for the viewer based on the estimated motion vector.

8. The video control method according to claim 7, further comprising decreasing or increasing a speed of visual motion in the video in the direction comprised in the estimated motion vector.

9. The video control method according to claim 7, further comprising at least one of measuring a response of an autonomic nervous system of the viewer and evaluating a subjective response related to a physical condition of the viewer.

10. The video control method according to claim 7, further comprising stopping presentation of the video, displaying a still image, or presenting another video when the speed of the visual motion in the video comprised in the estimated motion vector exceeds a predetermined value.

* * * * *